(12) United States Patent
Tkacik et al.

(10) Patent No.: US 10,751,669 B2
(45) Date of Patent: Aug. 25, 2020

(54) ULTRAFILTRATION MEMBRANES AND METHODS OF MAKING

(71) Applicant: EMD Millipore Corporation, Burlington, MA (US)

(72) Inventors: Gabriel Tkacik, Bedford, MA (US); Philip Goddard, Merrimack, NH (US); Willem Kools, Reading, MA (US); Nitin Satav, Chelmsford, MA (US)

(73) Assignee: EMD MILLIPORE CORPORATION, Burlington, MA (US)

( * ) Notice: Subject to any disclaimer, the term of this patent is extended or adjusted under 35 U.S.C. 154(b) by 298 days.

(21) Appl. No.: 14/645,631

(22) Filed: Mar. 12, 2015

(65) Prior Publication Data
US 2015/0182913 A1 Jul. 2, 2015

Related U.S. Application Data

(60) Continuation of application No. 13/312,491, filed on Dec. 6, 2011, now Pat. No. 9,010,545, which is a (Continued)

(51) Int. Cl.
*B01D 69/12* (2006.01)
*B01D 67/00* (2006.01)
(Continued)

(52) U.S. Cl.
CPC .......... *B01D 69/12* (2013.01); *B01D 61/145* (2013.01); *B01D 67/0013* (2013.01);
(Continued)

(58) Field of Classification Search
CPC .... B01D 69/12; B01D 67/0016; B01D 71/68; B01D 67/0018; B01D 61/145;
(Continued)

(56) References Cited

U.S. PATENT DOCUMENTS

| 4,261,834 A | 4/1981 | deWinter |
| 4,824,568 A | 4/1989 | Allegrezza, Jr. et al. |

(Continued)

FOREIGN PATENT DOCUMENTS

| EP | 0245863 B1 | 11/1987 |
| EP | 0645174 B1 | 3/1995 |

(Continued)

OTHER PUBLICATIONS

Durapore Membrane Filters, EMD Millipore, Accessed Apr. 12, 2017, pp. 1-2.*

(Continued)

*Primary Examiner* — David C Mellon
(74) *Attorney, Agent, or Firm* — Troutman Pepper Hamilton Sanders LLP (Rochester)

(57) ABSTRACT

The present invention is an integral multilayered composite membrane having at least one ultrafiltration layer made by cocasting or sequentially casting a plurality of polymer solutions onto a support to form a multilayered liquid sheet and immersing the sheet into a liquid coagulation bath to effect phase separation and form a multilayered composite membrane having at least one ultrafiltration layer.

13 Claims, 5 Drawing Sheets

Related U.S. Application Data division of application No. 11/479,908, filed on Jun. 30, 2006, now abandoned.

(51) Int. Cl.

| | | |
|---|---|---|
| *B01D 71/34* | (2006.01) | |
| *B01D 61/14* | (2006.01) | |
| *C07K 1/34* | (2006.01) | |
| *B01D 71/68* | (2006.01) | |

(52) U.S. Cl.
CPC ..... *B01D 67/0016* (2013.01); *B01D 67/0018* (2013.01); *B01D 71/34* (2013.01); *B01D 71/68* (2013.01); *C07K 1/34* (2013.01); *B01D 2323/12* (2013.01); *B01D 2323/42* (2013.01); *B01D 2325/022* (2013.01)

(58) Field of Classification Search
CPC ................ B01D 71/34; B01D 67/0013; B01D 2323/12; B01D 2325/022; B01D 2323/42; C07K 1/34

See application file for complete search history.

(56) References Cited

U.S. PATENT DOCUMENTS

| | | | |
|---|---|---|---|
| 5,017,292 | A | 5/1991 | DiLeo et al. |
| 5,221,479 | A | 6/1993 | Etoh et al. |
| 5,228,994 | A | 7/1993 | Tkacik et al. |
| 5,246,647 | A | 9/1993 | Beck et al. |
| 5,444,097 | A | 8/1995 | Tkacik |
| 5,472,607 | A * | 12/1995 | Mailvaganam ........ B01D 69/08 210/490 |
| 5,620,790 | A | 4/1997 | Holzki et al. |
| 5,626,760 | A | 5/1997 | Pouchoulin |
| 5,736,044 | A | 4/1998 | Prouix et al. |
| 6,146,747 | A | 11/2000 | Wang et al. |
| 6,273,271 | B1 | 8/2001 | Moya |
| 6,706,184 | B2 | 3/2004 | Sale et al. |
| 7,108,791 | B2 | 9/2006 | Tkacik et al. |
| 9,010,545 | B2 | 4/2015 | Tkacik et al. |
| 9,010,546 | B2 | 4/2015 | Tkacik et al. |
| 9,592,474 | B2 | 3/2017 | Tkacik et al. |
| 9,908,086 | B2 | 3/2018 | Tkacik et al. |
| 10,118,133 | B2 | 11/2018 | Tkacik et al. |
| 2002/0063093 | A1 | 5/2002 | Rice et al. |
| 2002/0113006 | A1 | 8/2002 | Sale et al. |
| 2002/0175124 | A1 | 11/2002 | Tkacik |
| 2003/0217965 | A1 | 11/2003 | Kools |
| 2004/0023017 | A1 | 2/2004 | Nagoya et al. |
| 2007/0084788 | A1 | 4/2007 | Moya et al. |

FOREIGN PATENT DOCUMENTS

| | | |
|---|---|---|
| JP | 62-19205 A | 1/1987 |
| JP | 4-505579 A | 10/1992 |
| JP | 7-071624 B | 8/1995 |
| JP | 11-047561 A | 2/1999 |
| JP | 2002-516743 A | 6/2002 |
| JP | 2003-012693 A | 1/2003 |
| JP | 2003-509189 A | 3/2003 |
| JP | 2003-534408 A | 11/2003 |
| WO | 2001/019506 | 3/2001 |
| WO | 2001/089673 A2 | 11/2001 |
| WO | 2003/066202 | 8/2003 |
| WO | 2003/106545 A1 | 12/2003 |

OTHER PUBLICATIONS

Reclamation: Managing Water in the West, U.S. Department of the Interior Bureau of Reclamation, Sep. 20, 2010, pp. 1-3.
Swinyard et al., "Phase Separation in Non-Solvent/Dimethylformamide/Polyethersuphone and Non-Solvent/Dimetylformarnide/Polysulphone Systems," Brit. Pol. J. 20:317-321 (1998).
Encyclopedia fo Polymer Science and Engineering, vol. 9, John Wiley and Sons, 1987, pp. 512.
European Search Report for European Patent Application No. 05253940.0 (dated Dec. 12, 2005).
European Search Report for European Patent Application No. 09176394.6 (dated Jan. 20, 2010).
Cheryan, "Ultrafiltration Handbook," Technomic Publishing Co., Chapter 26—Introduction and Definitions (Ultrafiltration), S. S. Kulkami, et al. Chapter 31—Definitions (Microfiltration) R. H. Davis, 1986.
Davis, "Membrane Handbook," Van Nostrand and Reinhold, 1992.
Kesting, "Synthetic Polymer Membranes: A Structural Perspective," John Wiley & Sons, 1985, pp. 44-45 and 60-61.
Koros et al., "Terminology for Membranes and Membrane Processes," Internat. Union of Pure and App. Chem. 68 (7):1479-1489 (1996).
Lonsdale, "The Growth of Membrane Technology," J. Memrane Sci. 10:81, 116-117 (1982).
Porter, "Selecting the Right Membrane," Chem. Eng. Sci. 71:55 (1975).
Pusch et al., "Synthetic Membranes. Preparation, Structure and Application," Angew, Chem. Int. Ed. Engl. 21:660-685 (1982).
Schweitzer, "Handbook of Separation Techniques for Chemical Engineers," 3d Ed., Section 2.1, "Membrane Filtration," M.C. Porter, McGraw-Hill 1996.
Tkacik et al., "A Rejection Profile Test for Ultrafiltration membranes and Devices," Biotechnol. 9:941-943 (1991).
Zeman et al., "Microfiltration and Ultrafiltration: Principles and Applications," Marcel Dekker pp. 13, 134-146, 1996.
European Extended Search Report for European Patent Application No. 15154626.4 (dated Aug. 5, 2015).
Communication Pursuant to Article 94(3) EPC for European Patent Application No. 15154626.4 (dated May 3, 2019).
Communication Pursuant to Article 94(3) EPC for European Patent Application No. 15154626.4 (dated Jan. 20, 2020).
Baker, Membrane Technology and Applications, 2004 2nd Edition, John Wiley and Sons, Ltd, pp. 15, 68-69 (2004).

\* cited by examiner

ULTRAFILTRATION MEMBRANES AND METHODS OF MAKING

The present application is a continuation of U.S. patent application Ser. No. 13/312,491, filed Dec. 6, 2011, which is a divisional of U.S. patent application Ser. No. 11/479,908, filed Jun. 30, 2006, which is related to U.S. Provisional Patent Application Ser. No. 60/686,363, filed on Jun. 1, 2005, and to U.S. Provisional Patent Application Ser. No. 60/583,209, filed on Jun. 25, 2004, the entire contents of which are incorporated herewith.

This invention provides for multilayered composite membranes having at least one ultrafiltration layer produced from at least two polymer solutions, and a novel method of manufacturing such membranes. The membranes are particularly suited for use in dead-end ultrafiltration.

BACKGROUND OF INVENTION

Ultrafiltration and microporous membranes are used in pressure-driven filtration processes. Practitioners in the field of separation processes by membranes easily differentiate between microporous and ultrafiltration membranes and generally distinguish between them based on their application and aspects of their structure. Microporous and ultrafiltration membranes are made, sold and used as separate and distinct products. Despite some overlap in nomenclature, they are separate entities, and treated as such in the commercial world.

Ultrafiltration membranes are primarily used to concentrate or diafilter soluble macromolecules such as proteins, DNA, starches and natural or synthetic polymers. In the majority of uses, ultrafiltration is accomplished in the tangential flow filtration (TFF) mode, where the feed liquid is passed across the membrane surface and those molecules smaller than the pore size of the membrane pass through (filtrate) and the rest (retentate) remains on the first side of the membrane. As fluid also passes through there is a need to recycle or add to the retentate flow in order to maintain an efficient TFF operation. One advantage of using a TFF approach is that as the fluid constantly sweeps across the face of the membrane it tends to reduce fouling and polarization of the solutes at and near the membrane surface leading to longer life of the membrane.

Microporous membranes are primarily used to remove particles, such as solids, bacteria, and gels, from a liquid or gas stream in dead-end filtration mode. Dead-end filtration refers to filtration where the entire fluid stream being filtered goes through the filter with no recycle or retentate flow. Whatever material doesn't pass through the filter is left on its upper surface.

Ultrafiltration membranes are generally skinned asymmetric membranes, made for the most part on a support which remains a permanent part of the membrane structure. The support can be a non-woven or woven fabric, or a preformed membrane.

Microporous membranes are produced in supported or unsupported form. Usually, the support has the membrane or a portion of the membrane formed in the support, rather than on the support, as in ultrafiltration membranes.

The early cellulosic, nylon and polyvinylidene fluoride microporous membranes were symmetric and for the most part, unskinned. Presently, some asymmetric microporous membranes are produced, and some of these are skinned.

While it would seem that the two types of membrane could be differentiated by pore size, this is not the case, as will be discussed below. The reasons for this are that they are used in different applications, requiring different characterization methods. None of the methods usually used give an absolute pore size measure, and different methods cannot be directly compared.

Despite the similarities between microporous membranes and ultrafiltration membranes, the history of their development is quite different. It is therefore not surprising that there is more than one accepted demarcation between them.

Microporous membranes were commercially developed from the work of Zsigmondy by Sartorius Werke (Germany) in 1929. These were what are now call "air cast" membranes made by evaporating a thin layer of a polymer solution in a humid atmosphere. These membranes were and still are symmetric and generally unskinned. Since they were used to remove or hold bacteria, they were rated by the bacteria size that would be retained. This method resulted in pore size ratings in microns.

A common method used to rate microporous membranes is the bubble point test. In this method, the microporous membrane is placed in a holder and saturated with a test liquid. Gas pressure is applied to one side of the membrane and the pressure is increased at a fixed rate. The appearance of the first stream of bubbles from the downstream side is a measure of the largest pore. At a higher pressure where the liquid is forced out of the majority of the pores, the foam all over point (FAOP) is reached. These are described in ASTM F316-70 and ANS/ASTM F316-70 (Reapproved 1976).

Ultrafiltration membranes (UF) are a spin-off of the reverse osmosis membrane development research of Leob and Sourirajan. Alan Michaels fixed 1965 as the time when the first rudimentary UF membranes and devices first appeared on the market. UF membranes are made by immersion casting methods and are skinned and asymmetric. The initial commercial applications were related to protein concentration and the membranes were rated by the molecular weight of the protein that they would retain, i.e., the molecular weight cutoff rating of the membrane (MWCO).

While membrane ratings based on testing with proteins is still done, a common method uses non-protein macromolecules having a narrow molecular weight distribution, such as polysaccharides (Dextrans) or polyethylene glycols. See for example, *A rejection profile test for ultrafiltration membranes and devices*, BIOTECHNOLOGY 9 (1991) 941-943.

As membrane applications were developed in the 1960's and 1970's, UF membranes expanded to larger pore sizes and microporous membranes (MF) to smaller pores sizes. As this occurred, practitioners began to differentiate between the two types of membranes. It is interesting from a historical perspective that the earliest literature referred only to ultrafiltration. Both Kesting *Synthetic Polymer Membranes A Structural Perspective*, Robert E. Kesting, John Wiley & Sons 1985 and Lonsdale "*The Growth of Membrane Technology*". K. Lonsdale, J. Membrane Sci. 10 (1982) 81 cite to Ferry's major review of 1936 in which ultrafiltration refers to both ultrafiltration and microfiltration membranes. Kesting states "The term ultrafiltration has changed its meaning over the years." In fact, even in a 1982 review Pusch *Synthetic Membranes—Preparation, Structure, and Application*, W. Pusch and A. Walch Angew. Chem. Int. Ed. Engl. 21 (1982) 660 uses ultrafiltration to denote sieving membranes of from $0.005\mu$ to $1\mu$. Kesting, in table 2.9 (pg 45) has UF as 10-1000 Angstroms, 0.01-0.1 microns, and MF as 1000-100.000 Angstroms, 0.1-10 microns.

A 1969 chart from Dorr-Oliver has microporous pore size ranging from $0.03\mu$ to over $10\mu$, and UF ranging from $0.002\mu$ to $10\mu$. A recent handbook chapter. *Handbook of Separation techniques for Chemical Engineers*—Third Edition, Section 2.1 Membrane Filtration, M. C. Porter, McGraw-Hill 1996 claims this "reflects confusion in the literature among MF, UF and RO." In 1975 Porter *Selecting the Right Membrane*, M. C. Porter, Chem. Eng. Sci. 71 (1975) 55 proposed that UF cover the range from 0.001 to 0.02 microns, and MF from 0.02 to 10 microns. Lonsdale referred to this in Reference 2 and Porter uses this definition again in reference 4.

Cheryan *Ultrafiltration Handbook*, M. Cheryan, Technomic Publishing Co. Chapter 26—Introduction and Definitions (Ultrafiltration) S. S. Kulkarni et al Chapter 31—Definitions (Microfiltration) R. H. Davis 1986 has both Porter's ranges for UF and MF (uncited) and a chart that appears to be from the Dorr-Oliver chart. In Membrane Handbook, Davis, Van Nostrand and Reinhold DATE Davis gives MF as 0.02-10 microns, and Kulkarni et al describe UF as 10 to 1000 Angstroms, 0.001-0.1 microns. Another example of pore size ranges is from the *Encyclopedia of Polymer Science and Engineering*, Volume 9 pg 512, John Wiley and Sons 1987 which has UF as from 0.01 to 0.1 microns and MF as from 0.1 to 10 microns. Zeman *Microfiltration and Ultrafiltration*, L. Zeman and A. Zydney, Marcel Dekker, Inc 1996, p 13 has a chart in which UF ranges from 0.001 to 0.1 micron and MF from about 0.02 to 10 microns.

With respect to the present invention, we will define ultrafiltration membranes as compared to microporous membranes based on the definitions of the International Union of Pure and Applied Chemistry (IUPAC), "*Terminology for membranes and membrane processes*" published in Pure Appl. Chem., 1996, 68, 1479.

"72. microfiltration: pressure-driven membrane-based separation process in which particles and dissolved macromolecules larger than 0.1 µm are rejected."

"75. ultrafiltration: pressure-driven membrane-based separation process in which particles and dissolved macromolecules smaller than 0.1 µm and larger than about 2 nm are rejected."

The definition for ultrafiltration membranes will be based on what they do, and how they do it. Ultrafiltration membranes are capable of concentrating or diafiltering soluble macromolecules that have a size in solution of less than about 0.1 micron and operating continuously in a tangential flow mode for extended periods of time, usually more than 4 hours and for up to 24 hours. Microporous membranes are capable of removing particles larger than 0.1 micron and being used in dead-end filtration applications. Microporous membranes generally allow soluble macromolecules to pass through the membrane.

Ultrafiltration membrane production methods by immersion casting are well known. A concise discussion is given in *Microfiltration and Ultrafiltration: Principles and Applications* Marcel Dekker (1996); L. J. Zeman and A. J. Zydney eds. These preparations are generally described to consist of the following steps: a) preparation of a specific and well controlled preparation of a polymer solution, b) casting the polymer solution in the form of a thin film onto a substrate, c) coagulating the resulting film of the polymer solution in a nonsolvent and d) optionally drying the ultrafiltration membrane.

The common form of ultrafiltration membranes is the asymmetric membrane, where the pore size of the membrane varies as a function of location within the thickness of the membrane. The most common asymmetric membrane has a gradient structure, in which pore size increases from one surface to the other. Asymmetric membranes are more prone to damage, since their retention characteristic is concentrated in a thin surface region or skin. A membrane skin is a thin dense surface penetrated by surface pores. It has been found, however, that increased productivity results from having the feed stream to be filtered contacting the larger pore surface, which acts to prefilter the stream and reduce membrane plugging.

Practitioners in the art of making ultrafiltration membranes, particularly asymmetric membranes, have found that membranes which contain large (relative to membrane pore size) hollow cavernous structures have inferior properties compared to membranes made without such hollow structures. These hollow structures are sometimes called "macrovoids", although other terms are used in the art. Practitioners striving for membranes of very high retention efficiency prefer to make membranes without such hollow structures.

Perhaps the most direct variation of the single layer structure is a multilayered unbonded laminate. While laminates can be made from layers of the same or different membranes, they have drawbacks. Each layer has to be made in a separate manufacturing process, increasing cost and reducing manufacturing efficiency. It is difficult to manufacture and handle very thin membranes, less than say 20 microns, because they deform and wrinkle easily. This adds to the inefficiency of producing a final product with thin layers. Unbonded laminates can also come apart during fabrication into a final filter device, such as a pleated filter, which will cause flow and concentration non-uniformities. Other methods of forming multilayered porous membrane structures are known. U.S. Pat. No. 4,824,568 describes a composite ultrafiltration membrane made by casting a thin ultrafiltration membrane onto a preformed microporous membrane. U.S. Pat. No. 5,228,994 describes a method for coating a microporous substrate with a second microporous layer thereby forming a two layer composite microporous membrane. These processes require two separate membrane forming steps, forming one on top of the other preformed membrane and are restricted by the viscosities of the polymer solutions that can be used in the process to prevent excessive penetration of casting solution into the pores of the preformed substrate.

In U.S. Pat. No. 5,620,790, a method of making a microporous membrane is described wherein the membrane is made by pouring out a first layer on a support of polymeric material onto a substrate and subsequently pouring out one or more further layers of a solution of polymeric material onto the first layer prior to the occurrence of turbidity in each successively immediate preceding layer, the viscosity of each immediately successive layer of a solution of polymeric material having been the same or less than that of the preceding layer. US Patent Application 20030217965, directed to microporous membranes, provides for a method of producing an integral multilayered porous membrane by simultaneously co-casting a plurality of polymer solutions onto a support to form a multilayered liquid sheet and immersing the sheet into a liquid coagulation bath to effect phase separation and form a porous membrane. U.S. Pat. No. 6,706,184 discloses a process for forming a continuous, unsupported, multizone phase inversion microporous membrane having at least two zones comprised of the acts of: operatively positioning at least one dope applying apparatus, having at least two polymer dope feed slots, relative to a continuous moving coating surface; applying polymer dopes from each of the dope feed slots onto the continuously moving coating surface so as to create a multiple layer polymer dope coating on the coating surface; subjecting the multiple dope zone layer to contact with a phase inversion producing environment so as to form a wet multizone phase inversion microporous membrane; and then washing and drying the membrane. In these structures, each layer or zone is a microporous membrane. US Patent Application 20040023017 describes a multilayer microporous membrane containing a thermoplastic resin, comprising a coarse structure layer with a higher open pore ratio and a fine structure layer with a lower open pore ratio, wherein said coarse structure layer is present at least in one membrane surface having a thickness of not less than 5.0µ, a thickness of said fine structure layer is not less than 50% of the whole membrane thickness, and said coarse structure layer and said fine structure layer are formed in one-piece. The fine structure is not skinned. This structure is formed from a single solution.

SUMMARY OF THE INVENTION

Figure 1:
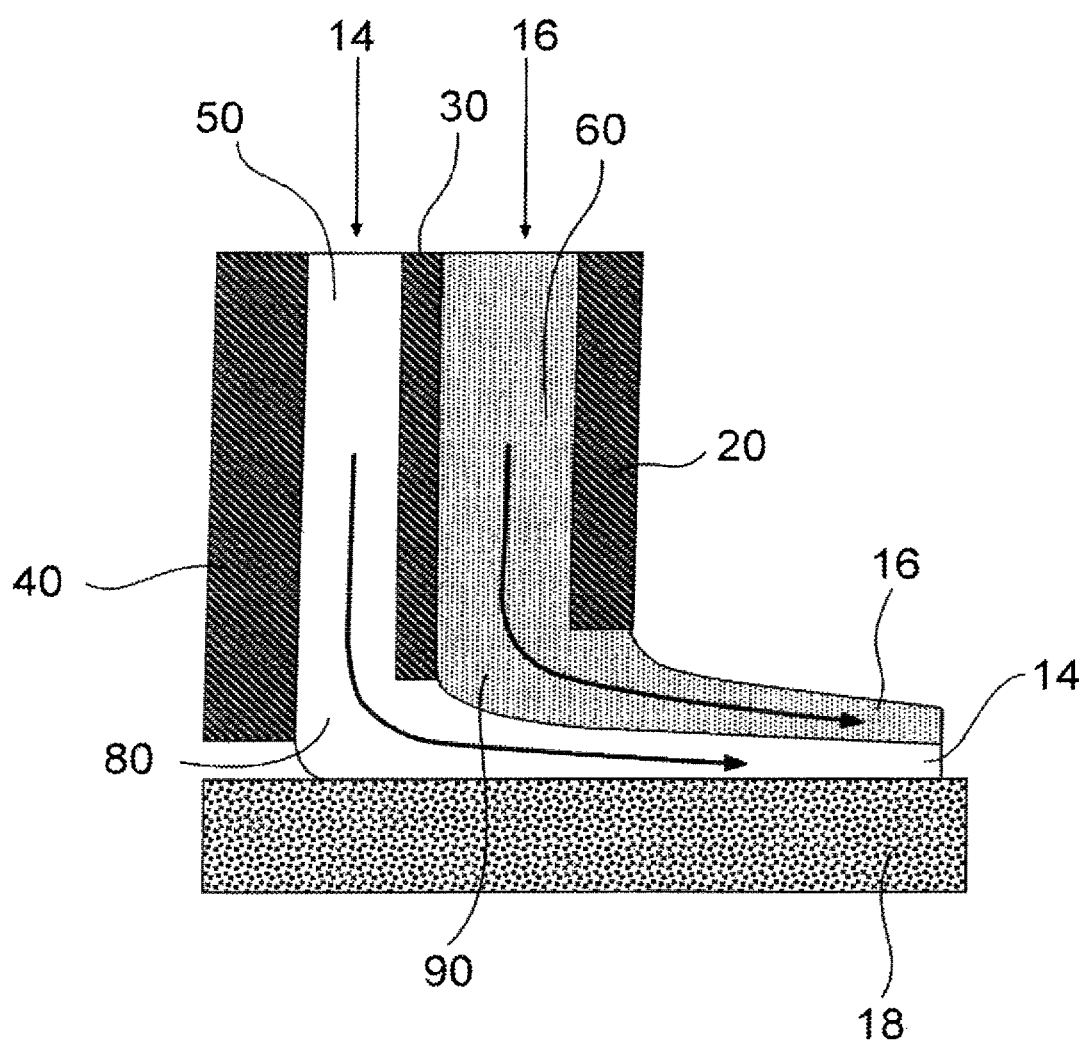
FIG. 1 illustrates a co-casting coating head.

This invention comprises an integral multilayer flat sheet membrane made from more than one polymer solution, wherein at least one layer is an ultrafiltration membrane. The method of making the membrane is included in the present invention.

In an embodiment, the invention comprises a skinned asymmetric ultrafiltration membrane layer joined to a microporous membrane layer, where the junction has a gradient of pore sizes, transitioning from the pore size of the microporous layer in the vicinity of the junction to the pore size of the ultrafiltration layer in the vicinity of the junction.

In an embodiment, the invention comprises a microporous membrane layer joined to the tight pore side of an ultrafiltration layer, where the junction has a gradient of pore sizes, transitioning from the pore size of the microporous layer in the vicinity of the junction to the pore size of the ultrafiltration layer in the vicinity of the junction.

In an embodiment, the invention comprises a skinned asymmetric ultrafiltration membrane layer joined to a second asymmetric ultrafiltration membrane layer, the second ultrafiltration membrane having an average retentive pore larger than that of the skinned asymmetric first layer, where the junction has a gradient of pore sizes, transitioning from the pore size of the second ultrafiltration layer in the vicinity of the junction to the pore size of the first ultrafiltration layer in the vicinity of the junction.

In an embodiment, the invention comprises a process for forming an integral multilayered composite ultrafiltration membrane compromising the steps of operatingly positioning a polymer solution applying apparatus having at least two dispensing outlets relative to a moving carrier surface, and; supplying each dispensing outlet with a different polymer solution, and; applying said solutions onto said moving carrier surface so as to create a multiple layer coating on said carrier, and wherein; said multiple layers are dispensed with essentially no time interval between successive layers being applied, and; subjecting said multiple liquid layers to a phase separation process so as to form a wet multilayer ultrafiltration membrane.

The invention further embodies the use of the membranes of the present invention in a process to remove viral particles from a manufactured protein-containing solution, made in the course of producing biotech derived pharmaceuticals, wherein the membranes is each capable of substantially preventing the passage therethrough of the virus particles and substantially permitting the passage therethrough of the protein.

DETAILED DESCRIPTION OF THE INVENTION

The present invention is an integral multilayered composite membrane having at least one ultrafiltration layer made by cocasting a plurality of polymer solutions onto a support to form a multilayered liquid sheet and immersing the sheet into a liquid coagulation bath to effect phase separation and form a porous ultrafiltration membrane. After formation, the porous membrane is washed free of solvent and other soluble materials. It can then be further extracted to reduce fugitive materials to a low level and then optionally be dried.

In order to reduce the present invention to practice, the inventors had to overcome the fundamental problem of making an integral multilayered structure from markedly dissimilar membrane-forming solutions. The inventors faced practical difficulties associated with the differences in structure and formation of the dissimilar membrane layers. While the prior art describes methods of making multilayered microporous membranes, in that art the membrane formulation solutions and mechanisms of membrane formation and membrane structure of each layer are quite similar.

In the present invention, pore size differences between the ultrafiltration (UF) layer and the microporous (MF) layer can differ by an order of magnitude. Also, the rate of formation of UF and MF membranes is different, with UF forming significantly faster in the coagulation bath. Potential and real problems that can arise with the fabrication of membranes of the present invention include:

If the last solution coated is a UF-forming solution, it may form too fast and too densely to permit the coagulation liquid to penetrating to the microporous forming layer at a rate necessary to form a satisfactory membrane. If the coagulant diffuses through the top layer too slowly, formation of the underlying microporous layer will be hindered, and pore size will be uncontrollable. As well, it may even occur that the underlying layer may not solidify before the coated sheet exits from the coagulant bath.

If the MF-forming solution is coated over the UF forming layer, the formation of the microporous layer will greatly affect the formation of the UF layer. It will prevent the formation of the skin surface, and change the pore size that would have resulted if the UF layer were cast separately.

Other problems can result from the disparity between viscosity ranges for the two types of membranes. UF membrane forming solutions are usually of much higher viscosity than those for MF membranes. Coating multilayers with viscosity discrepancies only exacerbates the problems of making porous membranes.

The inventors have found that within certain limited ranges on key variables, integral multilayer cocast composite ultrafiltration membranes with practical properties can be made.

For simplicity, the process of making a multilayer cocast composite ultrafiltration membrane will be described for a two layer example. Although three or more layers may also be made by the same process. The preferred process comprises the steps of making two polymer solutions, one for each layer. Solutions for making porous membranes by immersion casting usually comprise a polymer, solvent and additives to modify and control the final pore size and porous nature (i.e., percent porosity, pore size distribution, etc.) of the membrane. Other additives are sometimes used to modify physical properties such as hydrophilicity, elongation, modulus, etc.

Preferred polymers include but are not limited to polyvinylidene fluoride (PVDF), nylons such as Nylon 66, polyamides, polyimides, polyetherimides, polyethersulfones, polysulfones, polyarylsulfones, polyphenylsulphones, polyvinylchlorides (PVC), polycarbonates, cellulose, regenerated cellulose, cellulose esters such as cellulose acetate or cellulose nitrate, polystyrenes, acrylic polymers, methacrylic polymers, copolymers of acrylic or methacrylic polymers, or blends of any of the above and the like.

Solvents used include but are not limited to such examples as dimethyl formamide, N,N-dimethylacetamide, N-methyl pyrrolidone, tetramethylurea, acetone, dimethylsulfoxide and triethyl phosphate.

Examples of the many porogens have been used in the art, include but are not limited to compounds such as formamide, various alcohols and polyhydric compounds, water, various polyethylene glycols, polyvinyl pyrrolidone and various salts, such as calcium chloride and lithium chloride.

Examples of other additives include surfactants to improve wettability, and polymers compatible with the primary membrane polymer used to modify mechanical properties of the final membrane.

After the solutions are made, they are applied to a moving carrier. For an unsupported membrane, which does not have a web attached to the final membrane, the carrier is usually a plastic film, such as polyethylene terephtalate, or a polyethylene coated paper, or similar smooth continuous web that can be easily removed from the formed membrane.

Application can be done by any standard method. The object is to coat a first solution onto the carrier and a second solution upon the first solution. A highly preferred method is co-casting, in which the two layers are coated with essentially no time between coatings. This can be done with a double knife over roll apparatus a pressurized dual slot coating head or any other pre or postmetering coating device as is known in the industry. Co-casting means that the individual layers are cast essentially simultaneously with each other with substantially no time interval between one cast layer and the next cast layer. This method is described in detail in US published Patent Application 20030217965. Co-casting is an important aspect of the invention because it allows for formation of controlled pore size regions at the junctions of layers. In the prior art, a well-defined demarcation line is formed between the sequentially cast layers. A drastic change in pore size going from a more open to a more tight structure can lead to undesirable fast accumulation of retained solute at the interface and consequently a drastic flux decline. Possibly due to partial mixing of adjacent co-cast lacquers or due to high shear forces at the interface between two adjacent co-cast lacquers, a sharp interface can be replaced by a more subtle change in pore size between two adjacent layers with a cocast process. Such an interfacial zone is beneficial for the retentive behavior of the overall structure of the multilayered membrane and is therefore preferable in some applications. However even with the cocast technique one can, if desired, form a sharp or well-defined demarcation line between layers with the proper selection of materials and application methodologies.

The membranes of the present invention are preferably produced using a premetered coating process. Premetered coatings are those in which the exact amount of coating solution to be deposited is fed to the coating head. The height of the layers are set by the deposition rather than by some post application means such as a doctor blade which sets the thickness of the structure after metering of the layers (commonly referred to as "post metering process"). The premetered term is applied to die coating, slide and curtain coating among other methods of forming the structure. The present invention preferably uses a double knife box or double slot die. Post metered applications can also be used if desired.

FIG. 1 illustrates a multiple layer forming apparatus 10 for casting multilayered membranes. As shown, the apparatus is designed to produce a two-layered liquid film and has two chambers 50 and 60 containing the solutions 14 and 16, one for each layer, to be cast. If desired, additional chambers may be added to form additional co-cast layers. The apparatus comprises a front wall 20 and a back wall 40 with a separating wall 30 between the front and back walls. The separating wall defines the volumes of the two chambers. Two side walls, not shown, complete the apparatus. In operation, the apparatus is fastened onto a typical membrane casting machine, and a support web 18 is moved or passed under the stationary apparatus and the two solutions are dispensed through gaps or outlets 80 and 90. The thickness of the two layers is controlled by the distance (gap) set between the moving web and the outlet, illustrated by gap settings 80 and 90. The final liquid layer thickness is a function of gap distance, solution viscosities, and web speed. The back wall of the apparatus usually is held a small distance above the support to prevent wrinkling or marring the support. Back wall gap, support speed and solution viscosity are adjusted in practice to prevent solution from leaking out through the back wall gap. The apparatus can be fitted with heating or cooling means for each chamber separately, or for the apparatus as a whole, if necessitated by the solution characteristics, or to further control final membrane properties.

A slot die consists of an enclosed reservoir with an exit slot having a smaller cross-section. An extruder or positive displacement pump, or in some cases a pressurized vessel feeds the coating into the reservoir at a uniform rate, and all of the fluid that goes into the die is forced out from a reservoir through a slot by pressure, and transferred to a moving carrier web. The slot is positioned perpendicular to the moving carrier web. Multiple layer coatings require a die with individual reservoirs, and associated feed method, and exit slots for each layer.

After the layers are coated onto the moving carrier, the carrier with the liquid sheet is immersed into a liquid that is a nonsolvent for the polymer, and miscible with the solvent and porogens. This will cause phase separation and the formation of a porous membrane.

The formed composite membrane is then usually separated from the carrier and washed to remove residual solvent and other material. The membrane can then be dried. Ultrafiltration membranes are usually dried with a humectant, such as glycerine, by first immersing the washed membrane in an aqueous glycerine solution, of from 5% to 25% concentration by weight, and removing excess liquid, before proceeding through the drying step. Drying is done in a manner to remove the majority of the water and to leave sufficient glycerine to prevent pore collapse.

In the coagulation of a multilayered liquid sheet, coagulation occurs from the liquid film surface that first contacts the coagulation bath and then through the subsequent layers of the multilayered liquid sheet. Each layer dilutes and changes the coagulant as the coagulant diffuses through the layers. Such changes to the nature of the coagulant affect the membrane formation of each layer and of the final multilayer membrane. Layer thickness, composition and location of each layer relative to the other layers will affect membrane structure and properties. Each layer forms differently than it would if it were to be made from a single layer solution or from laminates of single layers.

In another embodiment, the two or more layers are sequentially cast successively on to the prior cast layer with some time between each cast so that some phase separation may occur in the earlier cast layer. All other steps of the process are the same as for those described with the cocast embodiment. This embodiment of sequential casting allows one to form UF containing structures similar to embodiments using only cocasting methods.

Figure 2A:
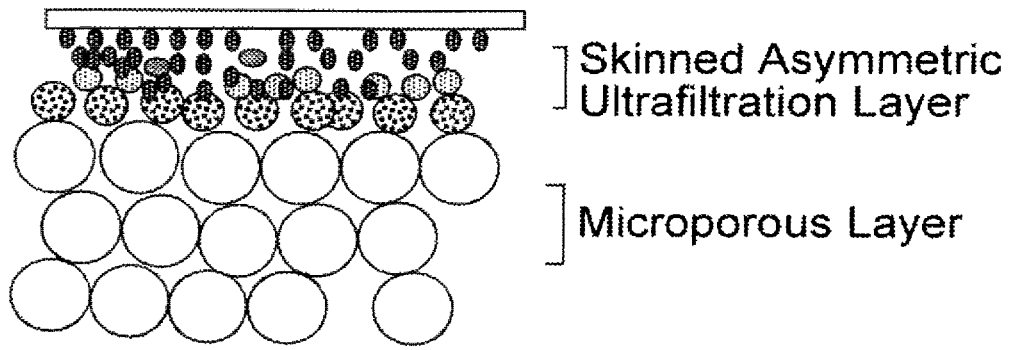
FIGS. 2a and 2b illustrate the position of the layers for two layer membranes.
Figure 2B:
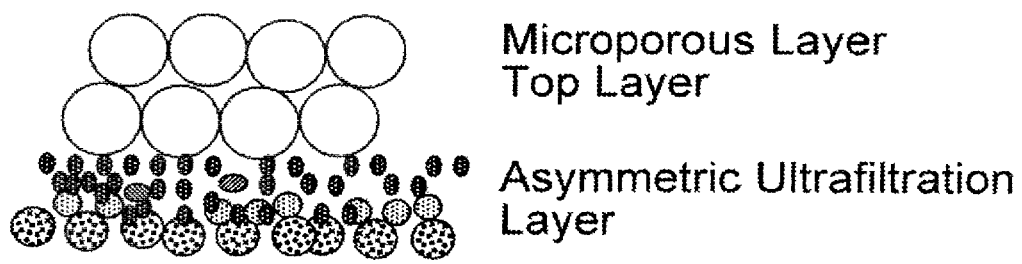

Reference is made to FIGS. 2a and 2b as an aid in the description of these multilayered membranes. It is common convention of those skilled in the art to denote as the "top surface" of an asymmetric membrane the facial surface having the smallest pore size. We will use this convention as a basis. For the case of multilayered membranes having an skinned asymmetric ultrafiltration membrane layer with no other layers contacting the skinned surface, the skinned asymmetric ultrafiltration membrane layer will be the first layer, or top layer, and subsequent layers numbered two, three, etc. This is illustrated in FIG. 2a. To be consistent, for the case where a microporous membrane is the top layer over an asymmetric ultrafiltration layer, the microporous layer will be denoted as the first layer, the ultrafiltration layer the second layer and so on. This is illustrated in FIG. 2b. Another manner of equivalently describing the nomenclature is to denote that the first side will be the top layer, i.e., the last solution coated onto the carrier, of the multilayered liquid sheet that has been cast.

The multilayered membrane of the present invention is not the same as an additive series of equivalently made single layer membranes. Due to the integral joining of the layers, there is a region where the pore size transitions from one layer to the next. To describe the structures, we will use the following device, with a two layer membrane as an example. A single layer membrane consists of a first side, a second side, and a porous structure between. Similarly, a laminate of two membranes would consist of a first layer with a first side, a second side, and a porous structure between, and a second layer with a first side, a second side, and a porous structure between. For a two layer membrane of the present invention, the first layer has a first side, and a second equivalent side. The second equivalent side would be a second side if this layer was a single layer membrane, but here it is part of the integral joining of the two layers. Likewise, the second layer has an equivalent first side and a second side and a porous structure between. The two equivalent sides are conjoined to form the conjoined thickness, that is, the transition zone between the two layers.

Asymmetric ultrafiltration membranes are sometimes used in dead-end filtration with the open or large pore surface at the upstream or high pressure side. An important application for such use is in removal of viral particles from process solutions in the manufacture of biotech therapeutic drugs. This is described in U.S. patent application Ser. No. 10/145,939.

The advantage of dead-end filtration lies in its simplicity. The pressurized feed stream is contacted with one side of the membrane and the fluid passes through while the material to be removed is retained by the membrane. In comparison, in tangential flow filtration (TFF), the pressurized feed stream is directed tangentially across the membrane face, and a portion of the feed stream passes through the membrane, while the remainder, the retentate, is usually recycled with added make-up feed, or returned to the feed tank. TFF requires extra pumping equipment, and more controllers to maintain the proper ratios of flows and pressure. However, dead-end filtration with ultrafiltration membranes has not been commonly used because the membranes tended to lose permeation properties too quickly to be useful.

The inventors have found that the multilayer ultrafiltration membranes of the present invention have greatly improved properties over prior art ultrafiltration membranes. The apparent reason for this improvement lies in the structure of the membranes, although no limitation should be put on the scope of the invention by the following discussion. It appears to the inventors that the pore size transition in the conjoining region plays a key role in the improved properties.

Figure 3:
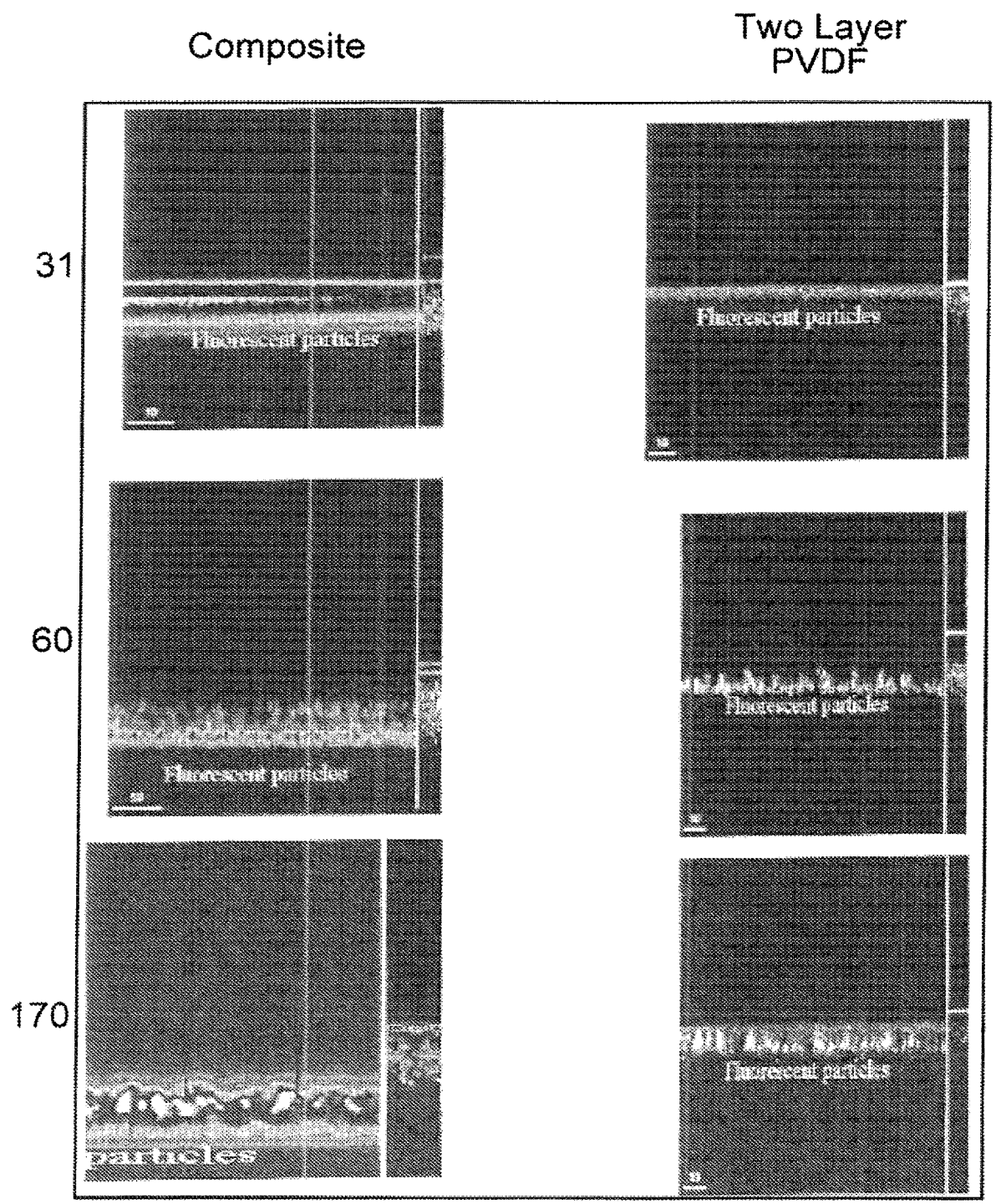
FIG. 3 shows results from filtration of fluorescent beads.

This is illustrated in FIG. 3 in which an example of a membrane of the present invention, a skinned asymmetric ultrafiltration membrane conjoined to a microporous layer, is compared to a two layer polyvinylidene fluoride (PVDF) ultrafiltration membrane made by casting an ultrafiltration layer on a pre-formed microporous membrane, (Viresolve® membrane available from Millipore Corporation of Billerica, Mass.).

FIG. 3 shows crossectional views of the membranes after having been used to filter fluorescent polystyrene beads from the open pore side in a dead-end mode. Three tests were done with bead sizes of 31 nm, 60 nm, and 170 nm.

For testing done with the 31 nm particles with the membrane of the present invention, the filtered particles are distributed throughout the thickness of the ultrafiltration layer. However, for the two layer PVDF, the particles are concentrated just under the small pore surface of the membranes. Since this surface provides the limiting pore size for flow, the concentrated particle layer will be more likely to plug these pores and will have a more deleterious effect on permeation.

For testing with the 60 nm particles, the particles are held away from the ultrafiltration layer and are diffusely distributed in the conjoining region. For the two layer PVDF, the particles form a concentrated layer near or at the junction of the microporous substrate and the ultrafiltration layer for the PVDF membrane.

Similar results are seen for the 170 nm particle testing. The membrane of the present invention retains the particles in a diffuse layer away from the skin. The two layer PVDF again traps the particles in a dense layer at the junction of the two layers.

In all these cases, the membrane of the present invention traps particles in a diffuse manner, which spread out the effects of pore plugging and increase filter flow and lifetime.

In an embodiment of the present invention, we use the teachings of U.S. Pat. No. 5,444,097 ('097) in a novel manner. The '097 patent teaches the use a polymeric solution exhibiting a lower critical solution temperature (LCST) to make microporous membranes. Heating an LCST solution above the LCST causes phase separation. This step is incorporated in the process of the present invention after the multilayered liquid film is formed to further vary and control the structures of the resulting membrane layers. One or several of the solutions of the present invention would be a LCST solution. It has been found that the temperature to which the solution is raised above the LCST, and the time the solution is held above LCST, controls the final pore size of the membrane layer. Furthermore, if there is a temperature gradient in a liquid layer, then there will be a corresponding pore size gradient.

In the present invention, the use of LCST solutions is used to produce a variety of structures.

For an bilayer composite ultrafiltration membrane made using LCST solutions having a first layer of a skinned asymmetric layer on a second microporous layer, a preferred solution for the first layer will have a polymer content of from about 15% to about 30% polymer solids, with a more preferred range of from about 20% to about 25% polymer solids. All percentages related to solutions are by % weight of the solution. For the microporous layer, the polymer solution will have a polymer content of from about 10% to about 20% polymer solids, with a more preferred range of from about 15% to about 18% polymer solids by weight of the solution. The LCST of the first layer solution is preferably from about 70° to about 150° C. For the second layer, the LCST range is preferably from about 40° to about 60° C. The thickness of the first layer is from about 2 microns to about 100 microns, preferably 2 microns to about 50 microns, with a more preferred range from about 2 microns to about 25 microns. The microporous second layer has a thickness range of from about 50 microns to about 200 microns, with a preferred thickness of from about 80 microns to about 150 microns, with a more preferred range of from about 100 microns to about 125 microns. It is preferable that the total thickness of the cocast composite membrane be in the range of from about 52 microns to about 300 microns, preferably from about 75 microns to about 200 microns, with a more preferred range of 90 microns to about 120 microns. If the pore size is determined by the temperature to which the LCST solution is raised above LCST, and the time maintained above LCST, the practitioner will determine by routine trial and error the proper conditions for operating their particular process equipment. Heating the solution can be done by several methods. The support coated with the polymer solution layers can be conveyed over a heated surface, such as a flat plate, a block, or a rod. A preferable method is to use a rotating heated drum. Heating can also be done by non-contact methods such as for example, infrared heating or microwave energy. If a heated drum is used to raise temperature of the coated web, the thickness and thermal insulating properties of the carrier web, and thickness of the polymer solution will be germane to obtaining a desired pore size. The temperature of the drum and the speed of the process will then be determined and controlled to produce the desired membrane. The temperature of the heated surface is determined by the equipment and the manufacturing process conditions as described above.

For the case of a microporous first layer and a second ultrafiltration layer, a preferred solution for the first layer will have a polymer content of from about 10% to about 20% polymer solids, with a more preferred range of from about 12% to about 16% polymer solids. All percentages related to solutions are by % weight of the solution. For the second ultrafiltration layer, the polymer solution will have a polymer content of from about 15% to about 30% polymer solids, with a more preferred range of from about 20% to about 25% polymer solids. The LCST of the first layer solution is preferably from about 40° to about 60° C. For the second layer, the LCST range is preferably from about 70° to about 120° C. The thickness of the first layer is from about 2 microns to about 50 microns, with a more preferred range from about 5 microns to about 25 microns. The ultrafiltration membrane second layer has a preferred thickness of from about 80 microns to about 150 microns, with a more preferred range of from about 100 microns to about 125 microns. It is preferable that the total thickness be in the range of from about 90 microns to about 120 microns. Similar to the above case, the practitioner will determine by routine trial and error the proper conditions for operating their equipment.

If it is desired to make two layers from ultrafiltration forming solutions, the parameters above will serve as guides to the individual layer compositions and process parameters.

In an embodiment, the first layer is formed from a solution and under conditions that would give a skinned asymmetric ultrafiltration membrane if cast as one layer. The second layer would give a microporous membrane if cast as one layer. The resulting structure is a skinned asymmetric ultrafiltration membrane on a microporous layer, with an integral transition zone between them. In a preferred method, both solutions from which the layers are cast have a LCST, with the ultrafiltration layer having a higher LCST. The cast multilayered liquid sheet is heated to a preplanned temperature above the LCST of the second (microporous) layer but below the LCST of the first (ultrafiltration) layer before immersion into the precipitation bath. This has been found to result in an ultrafiltration layer over a microporous layer with a transition zone between.

A preferred version of this embodiment can be done where the ultrafiltration layer does not have a LCST, or does not have a measurable LCST, while the microporous layer solution has a LCST, and the same general structure will result.

It is also possible to use two solutions, neither of which have a LCST, but which individually would make the combination of ultrafiltration and microporous layers required.

In an embodiment illustrated by Example 3, the membrane is formed from a top layer ultrafiltration membrane made from a solution with an LCST higher than the drum temperature used to heat the formed solution layers before immersion, and a bottom layer made from a solution having an LCST lower than the drum temperature. In this example, the LCST of the UF layer solution is assumed to be greater than 150° C. because it could not be measured due to limitations of the test equipment. Surprisingly, as the drum temperature approximately equals the LCST of the microporous layer solution, the gradient between the two layers becomes less observable. However, the composite membrane so-formed out-performs a two layered membrane made by casting an ultrafiltration layer on a preformed microporous membrane (Viresolve, Millipore Corporation). Without being limited by the following, it is the inventors present theory that the Viresolve membrane-making process results in interpenetration of the top layer into the bottom layer, which gives the type of results discussed in relation to FIG. 3. However, the membrane of Example 3, because it is formed in a single step, does not have the same type of "bottleneck" at the interface of the two layers. In fact, it has a gradient, which, albeit sharp, still functions as described herein as a membrane of the present invention.

In an embodiment, the first layer is a microporous layer preferably thin, that is, between 5 to 30 microns thick, and the second layer is made from a solution and under conditions that would produce an ultrafiltration layer. In a highly preferred embodiment, the microporous and ultrafiltration layers are produced from solutions having a LCST, with the LCST of the ultrafiltration layer solution being higher. When heated above the LCST of the microporous layer solution, but below that of the ultrafiltration layer solution, the microporous layer will phase separate. Subsequent immersion will fix the microporous structure and cause phase separation of the ultrafiltration solution to form the multi-layered membrane. A preferred version of this embodiment can be done where the ultrafiltration layer does not have a LCST, while the microporous layer solution has a LCST, and the same general structure will result. It is also possible to use two solutions, neither of which have a LCST, but which individually would make the combination of ultrafiltration and microporous layers required.

In an embodiment, the multilayered ultrafiltration membrane is made of two layers of ultrafiltration membrane-making solutions that would, if cast as single layers, produce skinned asymmetric ultrafiltration membranes.

In a similar manner, solutions with an upper critical solution temperature (UCST) which phase separate when cooled below the UCST can be used to make the inventive membranes, are formed into a multilayered liquid film in a heated state and cooled to obtain phase separation. In both the LCST and UCST embodiments, further phase separation can be provided by immersion into a coagulant, as described previously.

Control of the transition zone or region is important for the present invention. In order to get a useful transition zone, the inventors have found that it is desirable to control the thickness of each layer, in particular the first layer, as well as the relative viscosities of the two solutions, so that the viscosity difference is not too great, and the relative time of formation, that is, solidification, of the layers. The variables above will serve as a guideline for other practitioners, but it must be appreciated that for each set of solutions and the particular equipment used, there may be differences from those stated within the present description.

The present invention provides a high-resolution membrane-based method for removing a virus from a manufactured protein-containing solution, the method being particularly characterized by its capacity to be performed quickly (i.e., as measure by flux) and efficiently (i.e., as measured by log reduction value, LRV).

Conduct of the methodology involves flowing a manufactured protein-containing solution through a filtration device containing the composite ultrafiltration membranes of the present invention under conditions sufficient to effect passage of said protein through said composite membranes, and whereby any specifically-targeted virus contaminating said protein-containing solution, is substantially prevented from passing through said asymmetric membranes, is thereby substantially removed from the solution.

A "manufactured protein-containing solution" as used herein is a term of specific definition. In contrast to a solution having naturally-occurring protein content (e.g., water having naturally-occurring microbial content), the protein content in a "manufactured" solution will be enriched, as a result of human intervention and possible conduct of other solution refinement processes, such that the predominant solute in said solution is said protein.

In respect of the composite membranes, several criteria need to be present to perform the inventive methodology. First, each must be substantially hydrophilic. econdly, the composite membranes must be capable of substantially preventing the passage therethrough of the targeted virus, whilst substantially permitting the passage therethrough of the bio-manufactured protein.

Aside from, but relevant to, the virus removal methodology, the present invention also provides a filtration capsule comprising a pleated tube formed of one, two or three interfacially-contiguous composite ultrafiltration membranes. Although perhaps having applicability elsewhere, this product configuration has been found quite effective in the conduct of the inventive virus removal methodology, in respect of its durability, reliability, cost, and ease of use and replacement.

In light of the above, it is an objective of the present invention to provide a methodology for removing at a high resolution a virus from a manufactured protein-containing solution, and particularly, one capable of being performed effectively at a log reduction value of greater than 6 for a comparatively large virus (e.g., murine leukemia virus) or from a comparatively smaller virus (e.g., parvo virus).

It is another objective of the present invention to provide a filtration capsule useful for conducting said virus removal methodology.

It is another object of the present invention to provide a device for removing a virus from a solution, the device comprising a housing suitable for containing a filtration material and further characterized by an inlet for receiving fluid to be filtered and an outlet for removing filtrate, the filtration material comprising one, two or three composite void-free membranes, the upstream layer oriented such that its "tightest" side faces downstream.

In general, it has been found that by incorporation of multiple asymmetric ultrafiltration membranes, arranged in a pleated configuration with the membranes in "tight side down stream" orientation, the resulting filter capsule will have good viral retention capabilities, yet maintain good flux. Although these may not be as high without using all the teaching underlying the inventive methodology, such high degree of accomplishment (particularly with respect to viral retention) is not always required in all circumstances. For example, for certain non-pharmaceutical purification applications, log viral reduction values need not approach a value greater than 2.

As to its preferred structure, the filtration capsule comprises a tubular housing and a pleated filtration tube substantially co-axially enclosed within said housing. The tubular housing of the filtration capsule is constructed to contain and channel a fluid process stream conducted therethrough—and accordingly is provided with a fluid inlet and a filtrate outlet. The fluid process stream u, upstream of the pleated filtration tube, is introduced into the filtration capsule through the fluid inlet. Downstream of the pleated filtration tube, the fluid process stream d is released from the filtration capsule through filtrate outlet.

The materials used for the tubular housing will depend largely on its intended application. Injection-moldable thermoplastic materials such as polyethylene polypropylene and the like are the most likely candidates. However, the use of metals, glass, and ceramics are also contemplated. If sought for use in viral clearance of biopharmaceutical protein products, the material selected should be compatible with the fluids (e.g., solvents) and environmental parameters (e.g., temperature and pressure) involved therein, and should have low protein-binding characteristics. A preferred material in this regard is polypropylene.

Because filtration devices, in general, often need to satisfy several structural and functional criteria in the course of most filtration protocols, it is unlikely that its overall construction, including its housing and any internal components, will be simple. Although a single continuous and unitary structure is possible, in all likelihood the tubular housing will comprise several cooperating assembled parts which typically include a tubular housing that comprises an upper shell and one or two end caps.

The pleated filter tube is positioned within the tubular housing such that it will divide, in operation, the fluid process stream that flows between the fluid inlet and the filtrate outlet. The pleated filter tube is composed of at least one layer of the asymmetric membranes of the present invention. Preferably, the one or more layers are all oriented such that fluid introduced into said housing through the fluid inlet commences passage through each respective asymmetric membrane through its open-side.

The pleats of the filter tube can be configured in a corrugated shape or spirally positioned and can have a loop-shaped cross section or a folded cross-section, such as a W-shaped cross-section. As used herein, the term "pleat" or "pleated" is intended to include all such cross-sectional shapes. Relative to occupied volume, the pleated structure presents to an incoming fluid process flow more surface area than that which would be presented by use of flat sheet. This is of particular advantage in consideration of the desire to maximize flux, especially when dealing with high-resolution viral clearance protocols.

The pleated filter tube is packaged within a replaceable cartridge. While it is possible, at least conceptually, to place pleated filter tube within the filter capsule without the agency of a cartridge, replaceable or otherwise, in practice, commercial and environmental advantages are realized by allowing the possibility of easily replacing a spent pleated filter tube, without having to undergo burdensome and/or cumbersome dismantling procedures, and/or requiring disposal of an entire filter capsule. The replacement is performed by unscrewing end cap from upper shell, unplugging a spent filter cartridge from the filtrate outlet to which it is frictionally mated, plugging therein a fresh cartridge, and screwing the cap back on.

The one or more tubular pleated sheets are maintained in a relatively fixed tubular conformation within the filter capsule by use of the external and internal supports that together form the replaceable cartridge. These supports are made of rigid material and provided with uniformly dispersed holes to allow the inward flow i of fluid from regions peripheral to the pleated filter tube, through the membranes thereof into tube's core, and then ultimately out of filter capsule.

For further details regarding the construction and functions of a replaceable filter cartridge, reference can be made to U.S. Pat. No. 5,736,044, issued to S. Proulx et al. on Apr. 7, 1998. Among other subject matter, the patent describes a composite filter cartridge that includes both sheet membranes and depth filters. Aspects of such composite filter can be imported into the construction of the present filter capsule, without departing from the spirit and scope of the invention as defined herein.

To remove virus from a protein solution, a solution containing protein(s) of interest and one or more types of viruses and subjecting the solution to a filtration step utilizing one or more ultrafiltration membranes which can be conducted either in the TFF mode or the NFF mode. In either mode, the filtration is conducted under conditions to retain the virus generally having a 20 to 100 nanometer (nm) diameter on the membrane while permitting passage of protein(s) through the membrane. In addition, when filtration of the solution is completed, the membrane is flushed with water or an aqueous buffer solution to remove any retained proteins. The use of the flushing step permits obtaining high yield of protein solution substantially free of virus.

EXAMPLES

Cloud Point

The visual cloudpoint temperature is used to approximate the lower critical solution temperature for a polymeric solution of a given composition. This is the temperature at which a polymeric solution phase separates from one phase into two phases upon heating.

The procedure involves heating a small lacquer sample enclosed in a transparent container in a heating bath and observing the temperature at which the solution begins to turn cloudy. The procedure is performed slowly enough to ensure that the temperature indicated by a thermometer in the bath is the same as that in the lacquer sample.

Auto Ramp Bubble Point

The ABP Tester is an automated pressure-ramping device used for measuring bubble points on ultrafiltration and microporous membranes. The ABP bubble point is the "foam-all-over" pressure, visually observed by the operator.

Vmax

Vmax is a measure of the amount of solution membrane can filter before being plugged so that the flux is reduced to approximately zero flow. Vmax is measured by filtering a solution at a predetermined pressure and recording the volume filtered as a function of time. Time divided by volume is plotted versus volume. The inverse of the slope is Vmax.

Viral particle Retention Testing

Testing was carried out using a single 47 mm disk in a stainless steel holder (Millipore, Billerica, Mass.) cat # XX44 047 00) at a constant pressure of 30 psid, and data was collected automatically through a computer data acquisition package. Membranes were wet out with Milli-RO water (Millipore Corporation, Billerica, Mass.). All trials began with a buffer flush for 2-5 minutes to equilibrate the membrane and determine permeability. Membranes were run with their open pore side to the feed pressure. All candidates were tested with a solution containing 1 mg/mL human plasma IgG (Bayer, lot #648UO35) and $10^7$ pfu/mL Phi-X174 (Promega, cat # 11041m lot #7731801) in 10 mM acetate buffer, pH 5.0. Challenge particles of bacterial phage, Phi X 174 were assayed by a plaque assay using their host bacteria. A dilution series was generated to determine concentration. LRV was calculated as the negative logarithm of the ratio of permeate concentration to feed concentration.

Example 1

In the Examples, Solution Preparation was Done as Follows.

Polyethersulfone (PES) membranes were cast from a solution consisting of the polymer, Polyethersulfone (PES); Radel A200 resin (Solvay) solvent, N-methyl pyrrolidone (NMP) and non solvent, triethylene glycol (TEG). The solution was homogeneous at room temperature but phase separates when heated. The temperature at which the solution starts to phase separate called the cloud point temperature and was a function of the composition of the solution and extremely sensitive to the concentration of water. It is important to minimize the exposure of the raw materials, especially TEG, and the final solution to the atmosphere. The polymer was predried at for example 150° C. for three hours.

The mix was made in 2 steps. First, the polymer was added to a mixture of all the NMP and only part of the TEG. This portion was mixed while heated to between about 50° C. and 80° C. until the solution is clear. The temperature was lowered to between about 30° C. and about 50° C. The remaining TEG was then added to form the final solution.

A first polymer solution was prepared by dissolving 17% PES (Radel A200) in 29.2% NMP and 53.8% TEG. The resulting cloud point was 50.2° C.

A second polymer solution was prepared by dissolving 22% PES (Radel A200) in 28.1% NMP and 49.9% TEG. Additional NMP was added (6.3% of final solution) to arrive at a cloud point of 83.6° C.

The two solutions were co-cast as described in WO 01/89673 (Kools), using a slot die coater. The cast thickness of the first solution was adjusted to give a final layer thickness of 145 μm. The cast thickness of the second solution was adjusted to give a final layer thickness of 15 μm or about 10% of the overall membrane thickness.

The formation conditions are selected so that the first solution was quickly heated on the casting drum, a temperature above its cloud point, before the point of immersion into an aqueous immersion bath at 55° C. At the same time the second solution does not reach a temperature of its cloud point. As a result, a formation of a microporous layer resulted from the first polymer solution and a formation of an ultrafiltration layer resulted from the second polymer solution. The final membrane characteristics were varied by adjusting the drum temperature, and the thickness of the second layer was minimized in order to avoid undesirable macrovoid formation.

Figure 4A:
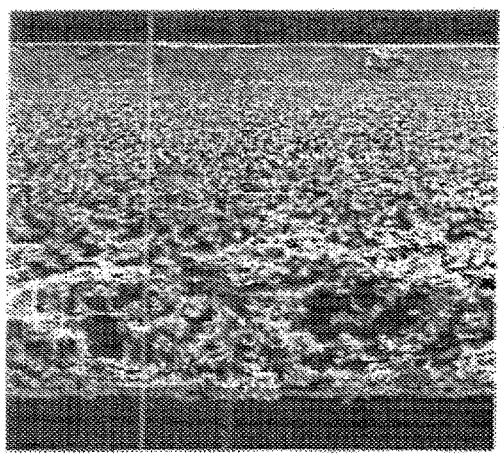
FIGS. 4a-4d show scanning electron micrograph images of the membranes of Examples 1 and 2.

The resulting structures and properties are shown below. The retentive nature is indicated by the high bubble point, while the void-free UF layer and dense UF surface can be clearly seen in the scanning electron microscope images (FIG. 4a. and FIG. 4b) (Drum temp 45° C. is shown). The transition from UF to MP is less clear, which could be advantageous for maximizing throughput.

| Sample | Drum Temp (° C.) | Bubble Point (psi) | Phi-X 174 Retention (LRV) |
|---|---|---|---|
| 1 | 58 | 102 | |
| 2 | 56 | 109 | 0.4 |
| 3 | 55 | 108 | 0.5 |
| 4 | 50 | 111 | 1.6 |
| 5 | 45 | 112 | 2.8 |

The data in the Table show increased virus retention with decreasing drum temperature. This effect of drum temperature is unexpected because the retentive UF layer has a LCST much above any of the drum temperatures used, and it is not expected that heating the UF solution to this degree would have any effect on membrane formation. However, as can be seen form the data, reducing the drum temperature from 58° C. to 45° C. increased virus retention by more than two orders of magnitude.

Sample 5 was compared to a two layer membrane made by casting an ultrafiltration layer onto a preformed microporous membrane to form a composite membrane with two distinct layers (Millipore PPVG membrane). The results below show that for similar permeability and BAP bubble points, the membrane of the present invention (Sample 5) had greatly improved Vmax properties and better virus removal.

| Membrane | ABP Bubble point | Flux liters/sq. meter/hr/psi | Phi-X LRV | Vmax |
|---|---|---|---|---|
| Sample 5 | 112 | 58 | 2.8 | 7717 |
| PPVG | 128 | 45.6 | 2.3 | 437 |

Example 2

A first polymer solution was prepared by dissolving 22% PES (Radel A200 resin) in 28.1% NMP and 49.9% TEG. The resulting cloud point was 48.6° C.

A second polymer solution was prepared by dissolving 14% PES (Radel A200 resin) in 29.2% NMP and 56.8% TEG. An additional 3% of NMP was added to arrive at a cloud point of 59.3° C.

The two solutions were co-cast as described in Example 1. The cast thickness of the first solution was adjusted to give a final layer thickness of 140 μm. The cast thickness of the second solution was adjusted to give a final layer thickness of 13 μm or 8% of the overall membrane thickness.

The formation conditions were selected so that the first solution was quickly exposed to the heated drum at 55° C., which was above its cloud point, before the point of immersion into an aqueous immersion bath at 45° C., which was below its cloud point. As a result, a formation of a macrovoid-free UF layer resulted from the first polymer solution and a formation of a thin microporous layer resulted from the second polymer solution.

Figure 4C:
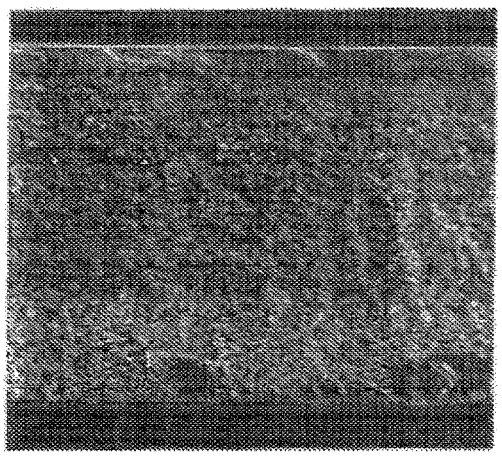
Figure 4B:
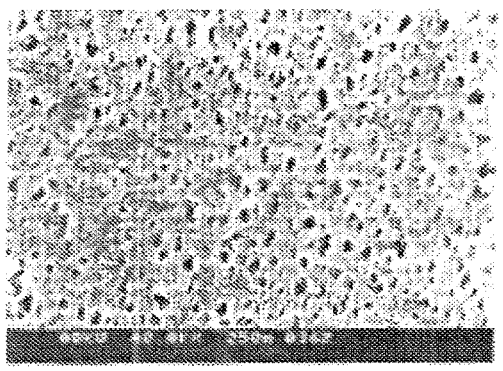
Figure 4D:
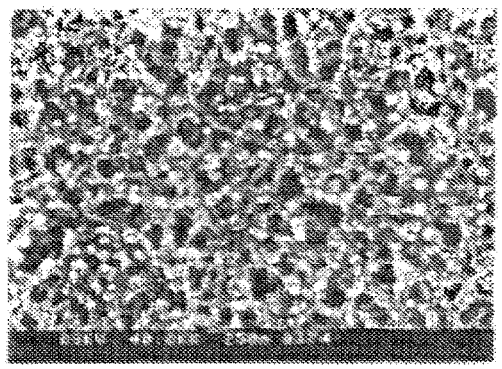
Figure 5:
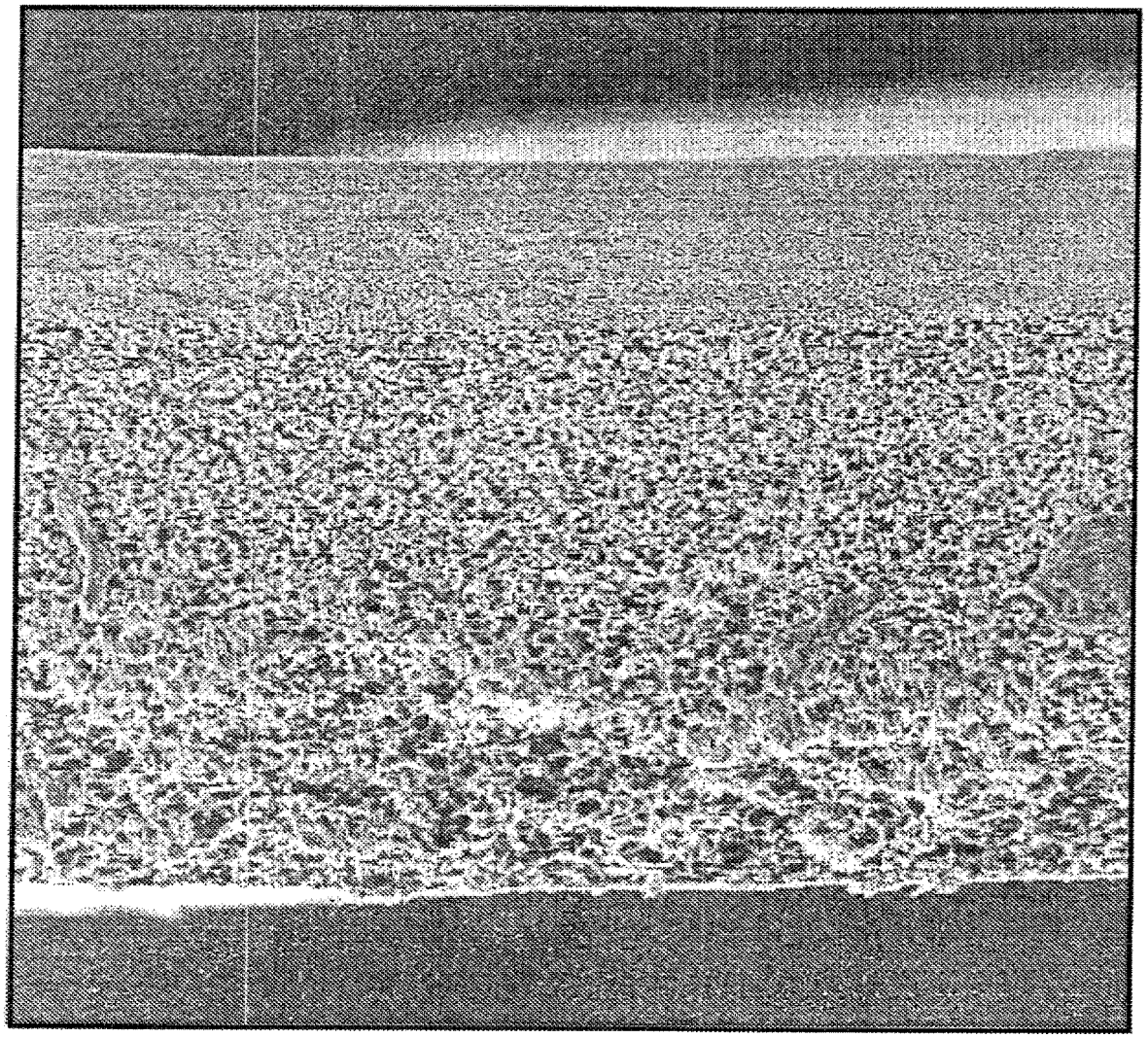
FIG. 5 shows scanning electron micrograph images of the membranes of Example 3.

The resulting bubble point was relatively high, and it is assumed that higher levels can be attained by additional variances in process conditions. The resulting structures are shown below, where the void-free UF layer and open MP surface can be clearly seen in the scanning electron microscope images (FIGS. 4c and 4d).

It was very surprising to the inventors that these conditions gave a membrane with no macrovoids and a very porous microporous surface. The drum temperature was above the LCST of the ultrafiltration layer, but below the LCST of the microporous layer. (Drum temperatures below the LCST of the ultrafiltration layer gave an ultrafiltration layer with voids.) However, the surface of the membrane of Example 2 showed a very high surface porosity.

Example 3

A first polymer solution was prepared by dissolving 17% PES (Radel A200) in 29.2% NMP and 53.8% TEG. The resulting cloud point was 43° C. This would be the bottom or support microporous layer.

A second polymer solution was prepared by dissolving 21% PES (Radel A200) in 37% NMP and 42% TEG. The cloud point could not be measured, being above 150° C. This would be the top ultrafiltration layer.

The two solutions were co-cast as described in WO 01/89673 (Kools). The second solution layered on the first solution. The cast thickness of the first solution was adjusted to give a final microporous membrane layer thickness of 160 μm. The cast thickness of the second solution was approximately 30 μm or about 20% of the overall membrane thickness.

The formation conditions were selected so that the layered solutions were quickly heated on the casting drum, at a range of temperatures around its cloud point, before the point of immersion into an aqueous immersion bath at 55° C. The second solution did not reach a temperature of its cloud point. As a result, a formation of a microporous layer resulted from the first polymer solution and a formation of an ultrafiltration layer resulted from the second polymer solution. The final membrane characteristics were varied by adjusting the drum temperature, and the thickness of the second layer was minimized in order to avoid undesirable macrovoid formation.

The resulting structure and properties are shown below. The retentive nature is indicated by the high retention, while the void-free UF layer and dense UF surface can be clearly seen in the scanning electron microscope image (Drum 50° C. is shown). The transition from UF to MP is more observable than in example 1, yet the resulting throughput was unaffected.

| Drum Temp (° C.) | Parvovirus Retention (LRV) | Vmax |
|---|---|---|
| 60 | 2.8 | 4110 |
| 55 | 3.7 | 2269 |
| 50 | 5.0 | 1119 |
| 45 | 5.1 | 228 |
| 40 | 5.5 | 204 |
| 35 | 2.7 | 75 |

As in Example 1, lowering the drum temperature increased virus retention. The LRV at 35° C. does not agree with the trend seen in other experiments. These conditions were repeated and the membrane produced had LRV of 5, and Vmax of ~20.

Example 4

A first polymer solution was prepared by dissolving 18% PES (Radel A200) in 30.2% NMP and 51.8% TEG. The resulting cloud point was 56° C. This would be the bottom or support microporous layer.

A second polymer solution was prepared by dissolving 23% PES (Radel A200) in 37% NMP and 42% TEG. The cloud point could not be measured, being above 150° C. This would be the top or ultrafiltration layer.

The two solutions were co-cast as described in WO 01/89673 (Kools). The second solution layered on the first solution. The cast thickness of the first solution was adjusted to give a final microporous membrane layer thickness of 155 µm. The cast thickness of the second solution was approximately 10 µm or about 6% of the overall membrane thickness.

The formation conditions were selected so that the layered solutions were quickly heated on the heated surface, at a range of temperatures around its cloud point, before the point of immersion into an aqueous immersion bath at 55° C. The second solution did not reach a temperature of its cloud point. As a result, a formation of a microporous layer resulted from the first polymer solution and a formation of an ultrafiltration layer resulted from the second polymer solution. The final membrane characteristics were varied by adjusting the surface temperature, and the thickness of the second layer was minimized in order to avoid undesirable macrovoid formation. The resulting properties were displayed below, showing both relatively high retention and high Vmax at the higher surface temperatures.

| Surface Temp (° C.) | Parvovirus Retention (LRV) | Vmax |
|---|---|---|
| 60 | 4.6 | 1774 |
| 55 | 4.5 | 1339 |
| 45 | 5.5 | 260 |

What is claimed:

1. A multilayered, flat sheet, composite membrane produced from at least two polymer solutions, the flat sheet membrane having at least one asymmetric ultrafiltration layer in which particles having a 20 to 100 nanometer (nm) diameter are retained and at least one asymmetric microporous layer in which particles larger than 0.1 µm are retained, wherein the polymer solutions include a first polymer solution that forms the at least one ultrafiltration layer and a second polymer solution that forms the at least one microporous layer, wherein the multilayered membrane has an integral transition zone between the at least one ultrafiltration layer and the at least one microporous layer, wherein the transition zone is a region comprising a gradient of pore sizes between the at least one ultrafiltration layer to the at least one microporous layer.

2. The multilayered, flat sheet, composite membrane according to claim 1, wherein the ultrafiltration layer comprises a skinned, asymmetric ultrafiltration membrane layer.

3. The multilayered, flat sheet, composite membrane according to claim 1, wherein the second polymer solution has a lower critical solution temperature (LCST).

4. The multilayered, flat sheet, composite membrane according to claim 1, wherein both the first polymer solution and the second polymer solution have a lower critical solution temperature (LCST).

5. The multilayered, flat sheet, composite membrane according to claim 4, wherein the LCST of the first polymer solution is higher than the LCST of the second polymer solution.

6. The multilayered, flat sheet, composite membrane according to claim 1, wherein the polymers for the first and second polymer solutions are independently selected from the group consisting of polyvinylidene fluoride, nylons, polyamides, polyimides, polyetherimides, polyethersulfones, polysulfones, polyarylsulfones, cellulose, regenerated cellulose, cellulose esters, polystyrenes, acrylic polymers methacrylic polymers, copolymers acrylic methacrylic polymers, and combinations thereof.

7. The multilayered, flat sheet, composite membrane according to claim 1, wherein the ultrafiltration layer is 2 to 100 microns thick and the microporous layer is 50-200 microns thick.

8. The multilayered, flat sheet, composite membrane according to claim 1, wherein the ultrafiltration layer is 2 to 50 microns thick.

9. The multilayered, flat sheet, composite membrane according to claim 1, wherein the microporous layer is 80 to 150 microns thick.

10. The multilayered, flat sheet, composite membrane according to claim 1, wherein the membrane is 90 to 120 microns thick.

11. The multilayered, flat sheet, composite membrane according to claim 1, wherein the polymer solution that forms the at least one ultrafiltration layer has a polymer content of 15% to 30% polymer solids.

12. The multilayered, flat sheet, composite membrane according to claim 1, wherein the polymer solution that forms the at least one microporous layer has a polymer content of 10% to 20% polymer solids.

13. The multilayered, flat sheet, composite membrane according to claim 1, wherein the ultrafiltration membrane layer has pores sized to retain a parvo virus.

\* \* \* \* \*